(12) United States Patent
Donald et al.

(10) Patent No.: US 11,779,378 B2
(45) Date of Patent: Oct. 10, 2023

(54) SELF-ALIGNING PLATING SYSTEM AND METHOD

(71) Applicant: Medcom Advisors, LLC, Burlington, NC (US)

(72) Inventors: Gordon D Donald, Oceanport, NJ (US); Arthur A Alfaro, Holly Springs, NC (US)

(73) Assignee: Medcom Advisors, LLC, Holly Springs, NC (US)

( * ) Notice: Subject to any disclaimer, the term of this patent is extended or adjusted under 35 U.S.C. 154(b) by 100 days.

(21) Appl. No.: 16/740,936

(22) Filed: Jan. 13, 2020

(65) Prior Publication Data
US 2020/0289178 A1 Sep. 17, 2020

Related U.S. Application Data

(60) Provisional application No. 62/791,732, filed on Jan. 11, 2019.

(51) Int. Cl.
*A61B 17/80* (2006.01)
*A61F 2/44* (2006.01)
(Continued)

(52) U.S. Cl.
CPC ........ *A61B 17/808* (2013.01); *A61B 17/7059* (2013.01); *A61F 2/442* (2013.01);
(Continued)

(58) Field of Classification Search
CPC ... A61B 17/808; A61B 17/7059; A61B 17/58; A61B 2017/00477; A61F 2/442;
(Continued)

(56) References Cited

U.S. PATENT DOCUMENTS 6,120,503 A    9/2000 Michelson
6,613,091 B1 * 9/2003 Zdeblick ............... A61F 2/4637
                                              623/17.11
(Continued)

FOREIGN PATENT DOCUMENTS

CN    208823064 U    5/2019
KR    100989558 B1   10/2010
(Continued)

OTHER PUBLICATIONS

Medacts MectaLIF Anterior Interbody Fusion Device, Medacta International, available at <https://www.medacta.com/EN/mectalif-anterior>.
(Continued)

*Primary Examiner* — Jessica Weiss
(74) *Attorney, Agent, or Firm* — Dentons US LLP

(57) ABSTRACT

Self-aligning plating systems and methods are disclosed. The self-aligning plating system may include an interbody spacer, a medical device plate, and an insertion member. The interbody spacer may be inserted between a top vertebra and a bottom vertebra of a patient's spinal column. A medical device plate may slide along an insertion member in operable connectivity with the interbody spacer so that the medical device plate comes into contact with and can be secured to the patient's anatomy.

25 Claims, 7 Drawing Sheets

(51) Int. Cl.
*A61F 2/46* (2006.01)
*A61B 17/70* (2006.01)
*A61B 17/00* (2006.01)

(52) U.S. Cl.
CPC ... *A61F 2/4611* (2013.01); *A61B 2017/00477* (2013.01); *A61F 2002/4615* (2013.01); *A61F 2310/00011* (2013.01); *A61F 2310/00179* (2013.01); *A61F 2310/00359* (2013.01)

(58) Field of Classification Search
CPC ........ A61F 2/4611; A61F 2/46; A61F 2/4603; A61F 2002/4615; A61F 2310/00011; A61F 2310/00179; A61F 2310/00359
USPC ................ 623/17.11–17.16; 606/70–71, 99, 606/280–299, 86 A, 86 B, 914
See application file for complete search history.

(56) References Cited

U.S. PATENT DOCUMENTS

| | | | |
|---|---|---|---|
| 6,896,676 B2 | 5/2005 | Zubok et al. | |
| 7,238,203 B2 | 7/2007 | Bagga et al. | |
| 7,303,564 B2 | 12/2007 | Freid et al. | |
| 7,850,697 B2 | 12/2010 | Ross et al. | |
| 7,850,731 B2 | 12/2010 | Brittan et al. | |
| 8,070,816 B2 | 12/2011 | Taylor | |
| 8,100,955 B2 | 1/2012 | Blain et al. | |
| 8,100,971 B2 | 1/2012 | Trieu | |
| 8,172,854 B2 | 5/2012 | Blain et al. | |
| 8,187,329 B2 | 5/2012 | Theofilos | |
| 8,262,710 B2 | 9/2012 | Freedman et al. | |
| 8,323,343 B2 | 12/2012 | Michelson | |
| 8,343,219 B2 | 1/2013 | Allain et al. | |
| 8,343,223 B2 | 1/2013 | Bucci | |
| 8,454,694 B2* | 6/2013 | Armstrong | A61F 2/4611 623/17.11 |
| 8,500,811 B2 | 8/2013 | Blain et al. | |
| 8,535,378 B2 | 9/2013 | Jackson | |
| 8,840,667 B1 | 9/2014 | Tumialán | |
| 8,932,358 B1 | 1/2015 | Nehls | |
| 8,945,227 B2* | 2/2015 | Kirschman | A61B 17/70 623/17.16 |
| 9,180,022 B2 | 11/2015 | Georges et al. | |
| 9,220,609 B2 | 12/2015 | Mueller et al. | |
| 9,326,861 B2 | 5/2016 | Iott et al. | |
| 9,375,237 B2 | 6/2016 | Keegan et al. | |
| 9,427,330 B2* | 8/2016 | Petersheim | A61B 17/8042 |
| 9,603,611 B2 | 3/2017 | Perry | |
| 9,642,723 B2 | 5/2017 | Cheng et al. | |
| 9,937,055 B1 | 4/2018 | Bernhardt, Jr. et al. | |
| 9,956,087 B2 | 5/2018 | Seifert et al. | |
| 9,968,464 B2 | 5/2018 | Tanaka et al. | |
| 9,987,142 B2 | 6/2018 | Mcconnell | |
| 10,034,764 B2 | 7/2018 | Kana et al. | |
| 10,045,797 B1 | 8/2018 | Walkenhorst et al. | |
| 10,143,499 B2 | 12/2018 | Milz et al. | |
| 10,182,851 B2 | 1/2019 | Robie et al. | |
| 11,273,058 B2* | 3/2022 | Ouidja | A61F 2/30749 |
| 2004/0193269 A1* | 9/2004 | Fraser | A61B 17/7059 623/17.11 |
| 2005/0085913 A1* | 4/2005 | Fraser | A61F 2/4455 606/279 |
| 2008/0027550 A1 | 1/2008 | Link et al. | |
| 2008/0294262 A1 | 11/2008 | Levieux | |
| 2008/0312742 A1 | 12/2008 | Abernathie | |
| 2009/0012529 A1* | 1/2009 | Blain | A61B 17/808 606/86 A |
| 2011/0190892 A1 | 8/2011 | Kirschman | |
| 2012/0136392 A1* | 5/2012 | Keegan | A61B 17/808 606/279 |
| 2012/0136442 A1* | 5/2012 | Kleiner | A61F 2/4455 623/17.11 |
| 2013/0060337 A1* | 3/2013 | Petersheim | A61F 2/447 623/17.16 |
| 2016/0235448 A1* | 8/2016 | Seex | A61B 17/808 |
| 2016/0296341 A1* | 10/2016 | Tatsumi | A61F 2/447 |
| 2017/0340358 A1* | 11/2017 | Bullard | A61B 17/1757 |
| 2018/0028329 A1 | 2/2018 | Suh et al. | |
| 2018/0338841 A1* | 11/2018 | Miller | A61F 2/4611 |
| 2018/0368992 A1 | 12/2018 | Zink et al. | |
| 2019/0167442 A1* | 6/2019 | Scott-Young | A61B 17/7059 |

FOREIGN PATENT DOCUMENTS

| | | |
|---|---|---|
| WO | 2010/054208 A1 | 11/2009 |
| WO | 2012/056119 A1 | 5/2012 |
| WO | 2017/175024 A2 | 1/2017 |
| WO | 2019/006476 A1 | 1/2019 |

OTHER PUBLICATIONS

Lanx Launches Epic Anterior Thoracolumbar Plating System, MedGadget (Feb. 24, 2011), available at <https://www.medgadget.com/2011/02/lanx_launches_epic_anterior_thoracolumbarjplating_system.html>.

Eisner, Walter, "Medtronic Claims Better Anterior Cervical Fusion System," (Oct. 22, 2014), available at <https://ryortho.com/breaking/medtronic-claims-better-anterior-cervical-fusion-system/>.

"Thoraco-Lumbar Interbody Fusion Cage/Lateral/Peak/With Lumbar Bone Plate," Zimmer, available at <https://www.medicalexpo.com/prod/zimmer/product-74894-862704.html>.

"Lumbar Interbody Fusion Cage / Anterior / With Lumbar Bone Plate / 1 Level Zuma Integra," Integra, available at <https://healthmanagement.org/products/view/lumbar-interbody-fusion-cage-anterior-with-lumbar-bone-plate-1-level-zuma-integra>.

* cited by examiner

SELF-ALIGNING PLATING SYSTEM AND METHOD

CROSS-REFERENCE TO RELATED APPLICATIONS

The present application claims the benefit of U.S. provisional application No. 62/791,732, filed on Jan. 11, 2019, the entire disclosure of which is incorporated by reference as if set forth in its entirety herein.

TECHNICAL FIELD

Embodiments of the present invention generally relate to medical devices and, more particularly but not exclusively, to medical devices for properly positioning interbody devices with respect to a patient's anatomy.

BACKGROUND

Medical devices are frequently misaligned with respect to a patient's anatomy during or after placement. Cervical and lumbar fusion plates, for example, are often not precisely cephalad and caudad. These imprecise alignments may often only be detected by postoperative x-rays, which may show these plates or other devices at varying degrees of alignment that are off-center with respect to the patient's anatomy. This is visually displeasing (e.g., as apparent from postoperative X-rays) and clinically sub-optimal.

These types of misalignments are generally due to obfuscated operative views of a patient's anatomy. For example, soft tissue and intraoperative bleeding may affect a surgeon's field of view of the patient's anatomy during device placement.

On the other hand, minimally invasive surgical approaches inevitably reduce visibility and cause the surgeon to lose his or her orientation of the applicable medical device and/or the patient's anatomy. While being fixated to the patient's anatomy, the plate itself may also obscure the surgeon's view of the patient's anatomy. The surgeon's operative proficiency, knowledge, experience, and skill may also impact their ability to properly align medical devices with respect to the patient's anatomy.

Existing techniques to address these issues generally require the surgeon to take radiographs to see the device's implanted orientation and then make adjustments thereto. The surgeon may be required to take multiple X-rays as well, which is expensive, time-consuming, and a hazard to the health of the patient, surgeon, and surgical team.

During subsequent adjustment(s), the medical device may shift while the surgeon is trying to fixate it. This is particularly true without the aid of a temporary fixation device. This adds surgical time, increases the risk of infection, and increases the potential for other intraoperative complications. While guidewires have been used in surgery for many years, they only assist in aligning a device to a target area.

The result of these above-discussed problems is that surgeons generally rely on manual or inexact approaches to align medical devices with respect to a patient's anatomy. Unfortunately, the medical community has generally accepted these clinically sub-optimal, time-consuming, and costly techniques.

A need exists, therefore, for systems and methods that overcome the disadvantages of existing techniques.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

In one aspect, embodiments described herein generally relate to a self-aligning plating system. The system includes an interbody spacer having a first gendered coupling mechanism; a medical device plate; and an insertion member, the insertion member having a second gendered coupling mechanism, wherein: the gender of the first gendered coupling mechanism is the opposite gender of the second gendered coupling mechanism, the interbody spacer is configured to be inserted between adjacent vertebrae of a spinal column, the insertion member is configured to be operably connected to the interbody spacer at the first and second gendered coupling mechanisms, the medical device plate is configured to slide over the insertion member and operably connect to the interbody spacer and align with the adjacent vertebrae, and after the medical device plate is attached to the adjacent vertebrae, the insertion member is configured to be detached from the interbody spacer and medical device plate at the first and second gendered coupling mechanisms.

In some embodiments, the insertion member is operably shaped to receive the medical device plate.

In some embodiments, the insertion member is operably shaped to receive the interbody spacer.

In some embodiments, the first gendered coupling mechanism is a female coupling mechanism.

In some embodiments, the first gendered coupling mechanism is a male coupling mechanism.

In some embodiments, the medical device plate is attached with at least one screw.

In some embodiments, the spacer is at least one of a plastic, ceramic, metal, autograft, or allograft spacer.

In some embodiments, the insertion member can be pinched to remove the insertion member from the spacer.

In some embodiments, the spacer is configured to be at least one of a cervical, thoracic, or lumbar spacer.

In some embodiments, the medical device plate can be in contact with a plurality of spacers simultaneously to fixate a plurality of vertebrae.

According to another aspect, embodiments, relate to a method of attaching a medical device plate and interbody spacer to a spinal column. The method includes inserting an interbody spacer between adjacent vertebrae of the spinal column, the interbody spacer having a first gendered coupling mechanism; operably connecting an insertion member to the interbody spacer, the insertion member having a second gendered coupling mechanism, wherein the gender of the first gendered coupling mechanism is the opposite gender of the second gendered coupling mechanism; sliding the medical device plate along the insertion member to position the medical device plate over the interbody spacer; aligning the medical device plate at the adjacent vertebrae; attaching the medical device plate to the adjacent vertebrae; and detaching the insertion member from the interbody spacer.

In some embodiments, the insertion member is operably shaped to receive the medical device plate.

In some embodiments the insertion member is operably shaped to receive the interbody spacer.

In some embodiments, the first gendered coupling mechanism is a female coupling mechanism.

In some embodiments, the first gendered coupling mechanism is a male coupling mechanism.

In some embodiments, the medical device plate is attached with at least one screw.

In some embodiments, the spacer is at least one of a plastic, ceramic, metal, autograft, or allograft spacer.

In some embodiments, the insertion member can be pinched to remove the insertion member from the spacer.

In some embodiments, the spacer is configured to be at least one of a cervical, thoracic, or lumbar spacer.

In some embodiments, the method further includes removing the insertion member from a hole in the medical device plate; exposing the hole in the medical device plate; and attaching the medical device plate to at least one vertebrae of the adjacent vertebrae at the exposed hole In some embodiments, the medical device plate can be in contact with a plurality of spacers simultaneously to fixate a plurality of vertebrae.

According to another aspect, embodiments relate to a self-aligning plating system, the system. The system includes an interosseous spacer having a first gendered coupling mechanism; a medical device plate; and an insertion member, the insertion member having a second gendered coupling mechanism, wherein the gender of the first gendered coupling mechanism is the opposite gender of the second gendered coupling mechanism; the interosseous spacer is configured to be inserted between two or more bone elements of a spinal column; the insertion member is configured to be operably connected to the interosseous spacer at the first and second gendered coupling mechanism; the medical device plate is configured to slide over the insertion member and operably connect to the interbody spacer and align with the two or more bone elements; and after the medical device plate is attached to the two or more bone elements, the insertion member is configured to be detached from the interosseous spacer and medical device plate at the first and second gendered coupling mechanisms.

BRIEF DESCRIPTION OF DRAWINGS

Non-limiting and non-exhaustive embodiments of this disclosure are described with reference to the following figures, wherein like reference numerals refer to like parts throughout the various views unless otherwise specified.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

The embodiments described herein provide novel self-aligning plating systems and methods. The disclosed systems may include an interbody spacer, a medical device plate, and an insertion member. In use, the interbody spacer is configured to be inserted between two portions of a patient's anatomy, such as between adjacent vertebrae of the patient's spinal column. This interbody spacer essentially serves as an alignment tool, onto which the medical device plate is positioned to contact the anatomy portion(s).

Figure 1A:
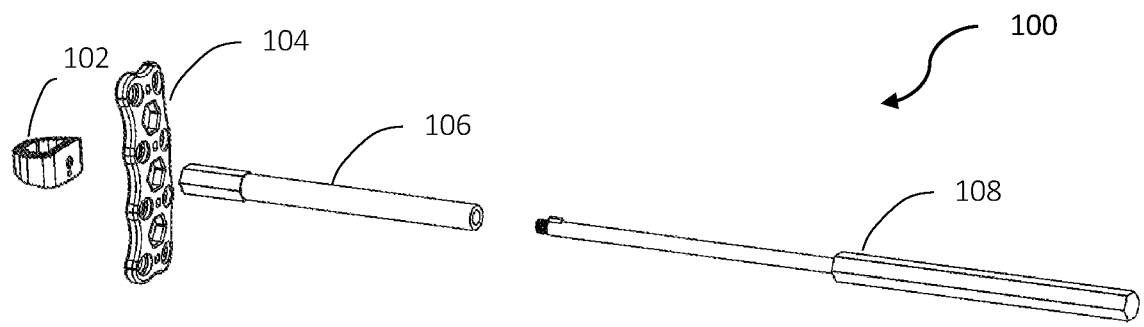
FIGS. 1A & 1B illustrate a self-aligning plating system 100 in accordance with one embodiment.
Figure 1B:
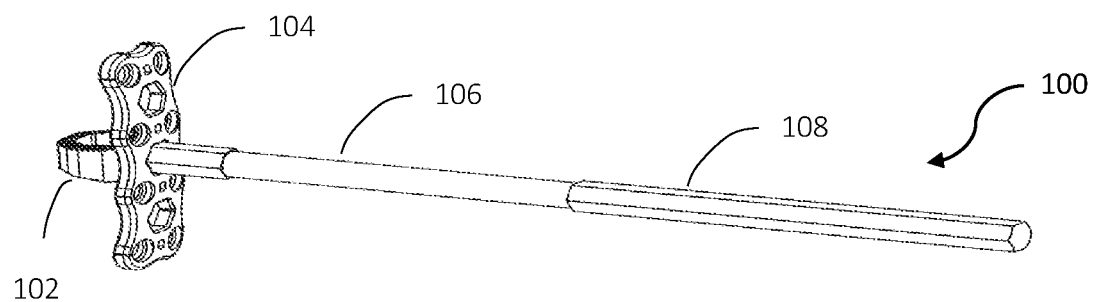

FIG. 1A illustrates an exploded view a self-aligning plating system 100 in accordance with one embodiment. As seen in FIG. 1A, the self-aligning plating system 100 may include an interbody spacer 102, a medical device plate 104, an insertion member 106, and an optional extension member 108 to operably engage the insertion member 106 during alignment/insertion. FIG. 1B illustrates the components of the self-aligning plating system 100 of FIG. 1A in contact with each other such as during placement of the interbody spacer 102 and the medical device plate 104.

The interbody spacer 102 may be made of plastic and include or otherwise be configured with a first gendered coupling mechanism, and the insertion member 106 may include or otherwise be configured with a second gendered coupling mechanism such that the interbody spacer 102 and the insertion member 106 can operably engage each other. The interbody spacer 102 may be a ceramic, metal, autograft, or allograft spacer in some embodiments. In some embodiments, the first gendered coupling mechanism may be a female coupling mechanism and the second gendered coupling mechanism may be a male coupling mechanism. In some embodiments, the first gendered coupling mechanism may be a male coupling mechanism and the second gendered coupling mechanism may be a female coupling mechanism. The exact configurations of the first and second gendered coupling mechanisms may vary as long as the interbody spacer 102 and the insertion member 106 can operably engage each other to accomplish the objectives of the embodiments described herein.

During placement, the interbody spacer 102 may be inserted between two portions of a patient's anatomy such as between a top and bottom vertebra. This placement may be facilitated by the insertion member via engagement between the above-discussed first and second gendered coupling mechanisms. The medical device plate 104 may then be positioned at one end of the insertion member 106, and slid over the insertion member 106 to eventually come into contact with the interbody spacer 102 and the patient anatomy portion(s).

The configuration of the interbody spacer 102, the medical device plate 104, and the insertion member 106 may vary as long as a surgeon can properly position the required components with respect to the patient's anatomy. For example, the medical device plate 104 may be configured with one or more hexagonal-shaped holes, and the insertion member 106 may include a hexagonal-shaped perimeter such that the medical device plate 104 can slide over the perimeter of the insertion member 106 to contact the interbody spacer 102.

FIGS. 2A-2D illustrate multiple views of an interbody spacer 202 in accordance with one embodiment. The interbody spacer 202 may be similar to the interbody spacer 102 of FIGS. 1A-1B, for example.

Figure 2A:
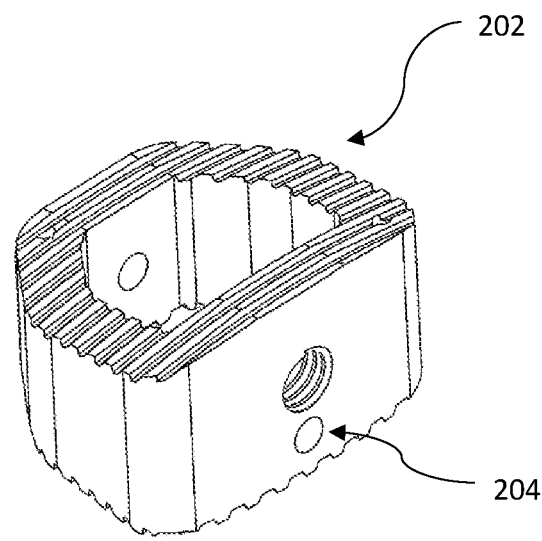
FIGS. 2A-2D illustrate the interbody spacer 102 of FIGS. 1A and 1B in accordance with one embodiment.
Figure 2B:
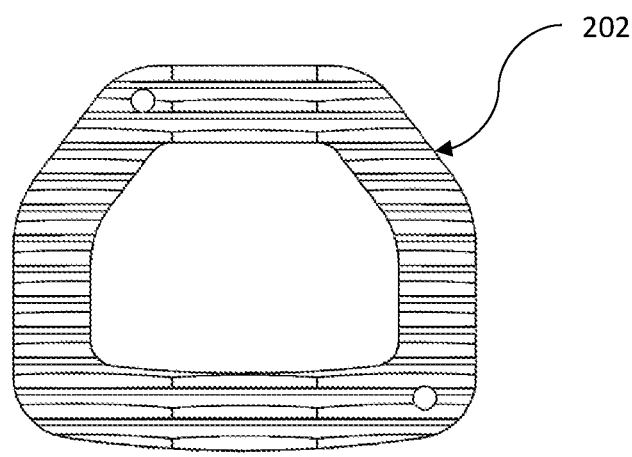
Figure 2C:
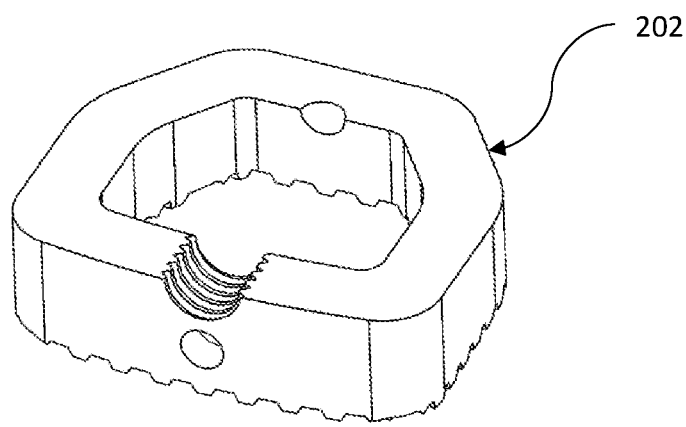
Figure 2D:
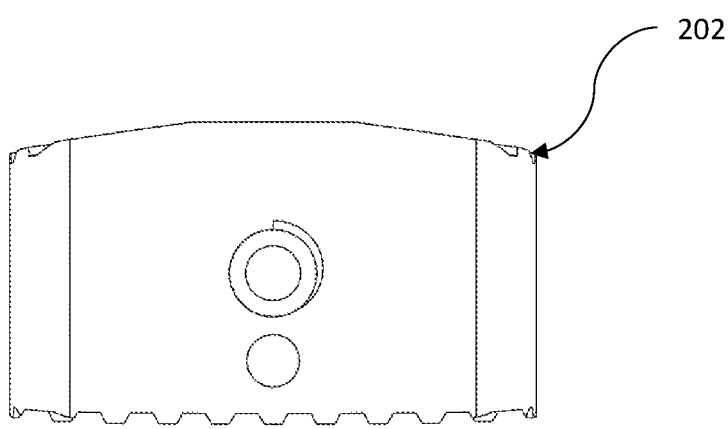

FIGS. 2A-2B illustrate perspective and top views of the interbody spacer 202, respectively. FIG. 2C illustrates a cross-sectional view of the interbody spacer 202 and FIG. 2D illustrates a front view of the interbody spacer 202. As seen in FIGS. 2A-2D, the interbody spacer 202 includes an alignment hole 204 to assist in aligning a plate such as the medical device plate 104 of FIGS. 1A-1B.

The alignment hole 204 may serve as a female coupling mechanism such that it can receive a male coupling mechanism of the insertion member 106. The alignment hole 204 may be formed of a plurality of threads such that it can receive a screw with threaded portions, for example.

Figure 3A:
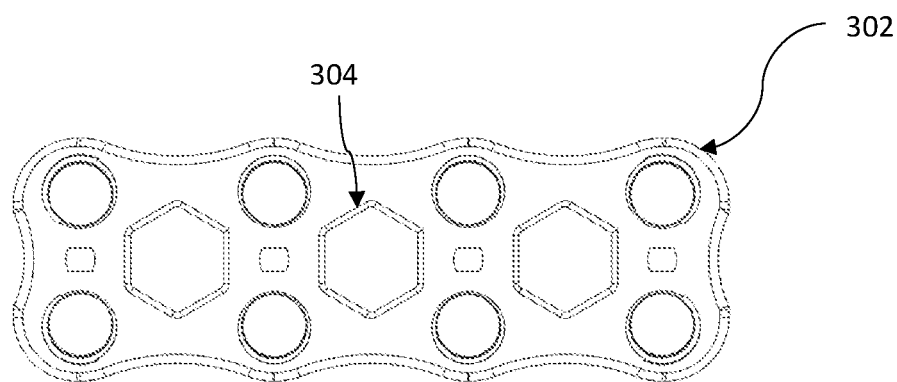
FIGS. 3A & 3B illustrate the medical device plate 104 of FIGS. 1A and 1B in accordance with one embodiment.
Figure 3B:
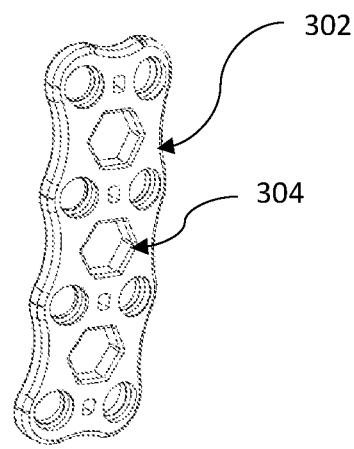

FIGS. 3A-3B illustrate a medical device plate 302 in accordance with one embodiment. As seen in FIGS. 3A-3B, the medical device plate 302 may include one or more alignment holes 304. In this particular embodiment, the alignment hole(s) 304 on the medical device plate 302 are hexagonal-shaped. The exact shape and size of the alignment hole(s) 304 on the plate 302 may vary as long they can receive the insertion member and operably connect to the interbody spacer for proper alignment with respect to the interbody spacer 102 and patient anatomy.

The plate may further include lines, groves, or some other indicia to indicate and achieve proper alignment. Once properly aligned with the interbody spacer, the medical device plate may be secured to the patient using any suitable technique(s).

In operation, and with reference to FIGS. 1A & 1B, a surgeon may place the interbody spacer 102 at an appropriate position with respect to a patient's anatomy. If the surgeon hadn't previously done so, he or she may then operably connect the insertion member 106 with the interbody spacer 102 (e.g., into an alignment hole of the interbody spacer 102 such as the alignment hole 204 of FIGS. 2A-2D).

Once the insertion member 106 is operably connected with the interbody spacer 102, the surgeon may place the medical device plate 104 on the insertion member 106 such that the insertion member 106 can then "pass through" a hole of the medical device plate 104. The surgeon may then slide the medical device plate 104 along the length of the insertion member 106 until it comes into contact with the patient's anatomy (e.g., adjacent vertebrae) and the interbody spacer 102. The medical device plate 104 would therefore be properly aligned with respect to the patient's anatomy in the correct coronal, axial, and sagittal orientations.

The insertion member 106 may serve as a temporary fixation of the plate to the patient's anatomy, such as before the medical device plate 104 is secured to the patient. This alignment can also be used for other surgical or medical templates/guides. For example, the insertion member 106 may be used to deliver organic and/or inorganic bone void/bone grafting materials or extenders.

Figure 4:
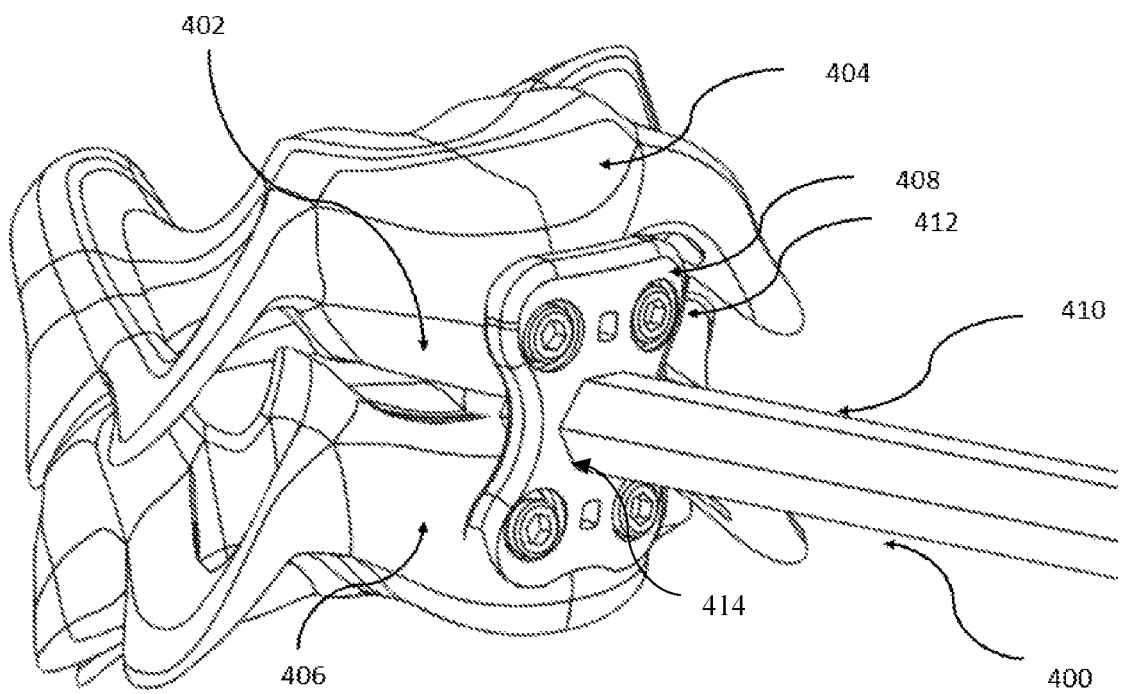
FIG. 4 illustrates a self-aligning plating system 100 secured to a patient in accordance with one embodiment.

FIG. 4 illustrates a self-aligning plating system 400 secured to a patient in accordance with one embodiment. In this embodiment, an interbody spacer 402 is positioned between a top vertebra 404 and a bottom vertebra 406 of a patient's anatomy. A medical device plate 408 that includes a hexagonal-shaped hole has been slid over an insertion member 410 to come into contact with the interbody spacer 402, the top vertebra 404, and the bottom vertebra 406. The medical device plate 408 has been secured to the top and bottom vertebra 404 and 406, respectively, by a plurality of screws 412. Once the medical device plate 408 is secured, the insertion member 410 may be detached from the interbody spacer 402.

Although only two vertebra are shown in FIG. 4, the medical device plate 408 may contact more than two vertebra. For example, there may be two interbody spacers operably positioned with respect to a patient's anatomy, such as a first interbody spacer positioned between a top vertebra and a middle vertebra, and a second interbody spacer positioned between the middle vertebra and a bottom vertebra. In this scenario, a medical device plate may contact each interbody spacer to fixate a plurality of vertebra.

In some embodiments, when the insertion member 410 is removed from the medical device plate 408, a hole 414 in the medical device plate 408 may be exposed. Once the hole 408 is exposed, the plate 410 may be secured to at least one vertebra or the interbody spacer 402. The medical device plate 408 may be secured with a screw, stake, nail, or other fixture in some embodiments.

Figure 5:
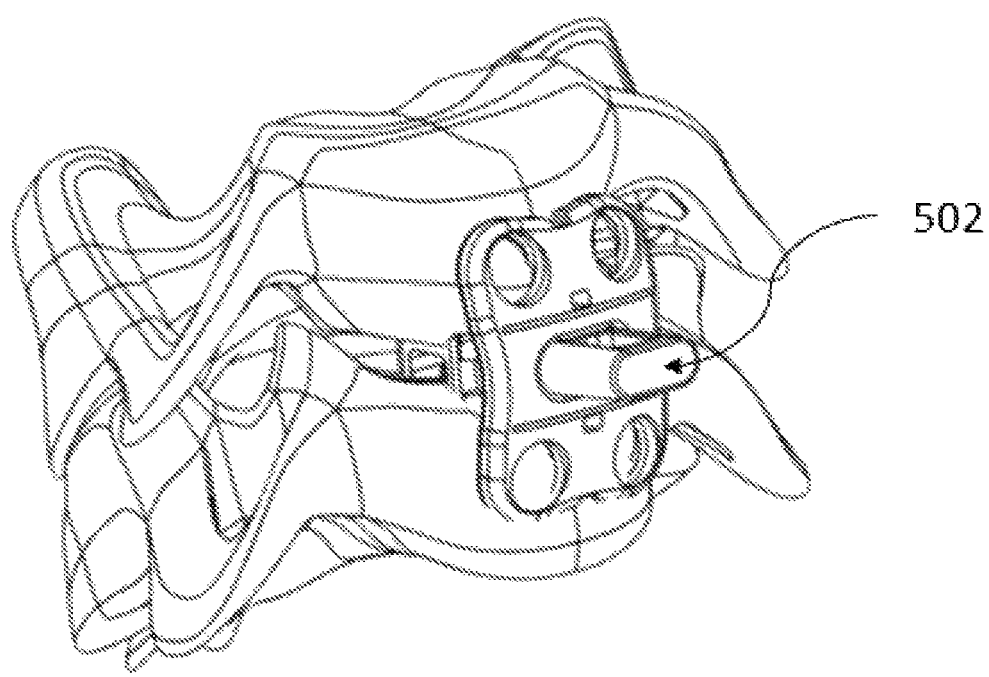
FIG. 5 illustrates a self-aligning plating system secured to a patient in accordance with another embodiment.
Figure 6:
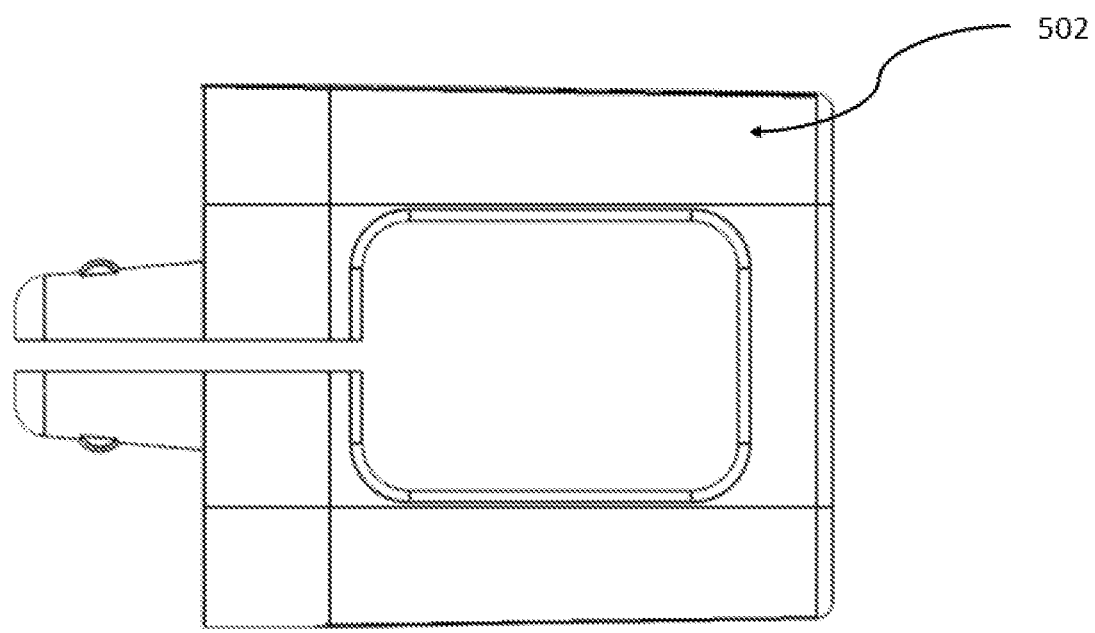
FIG. 6 illustrates the insertion member 502 of the self-aligning plating system of FIG. 5 in accordance with one embodiment.

FIG. 5 illustrates another embodiment in which the insertion member 502 is configured as a standalone component. FIG. 6 illustrates the insertion member 502 of FIG. 5 in accordance with one embodiment. Once the medical device plate has been secured to the patient, the surgeon may apply pressure to squeeze the insertion member 502 to disengage and detach the insertion member 502 from the patient (and the interbody spacer). In some embodiments, the insertion member 502 may be passively attached and detached from the interbody spacer. In some embodiments, the insertion member 502 may be actively attached and detached from the interbody spacer. For example, the insertion member 502 may be pinched to remove the insertion member from the interbody spacer.

Figure 7:
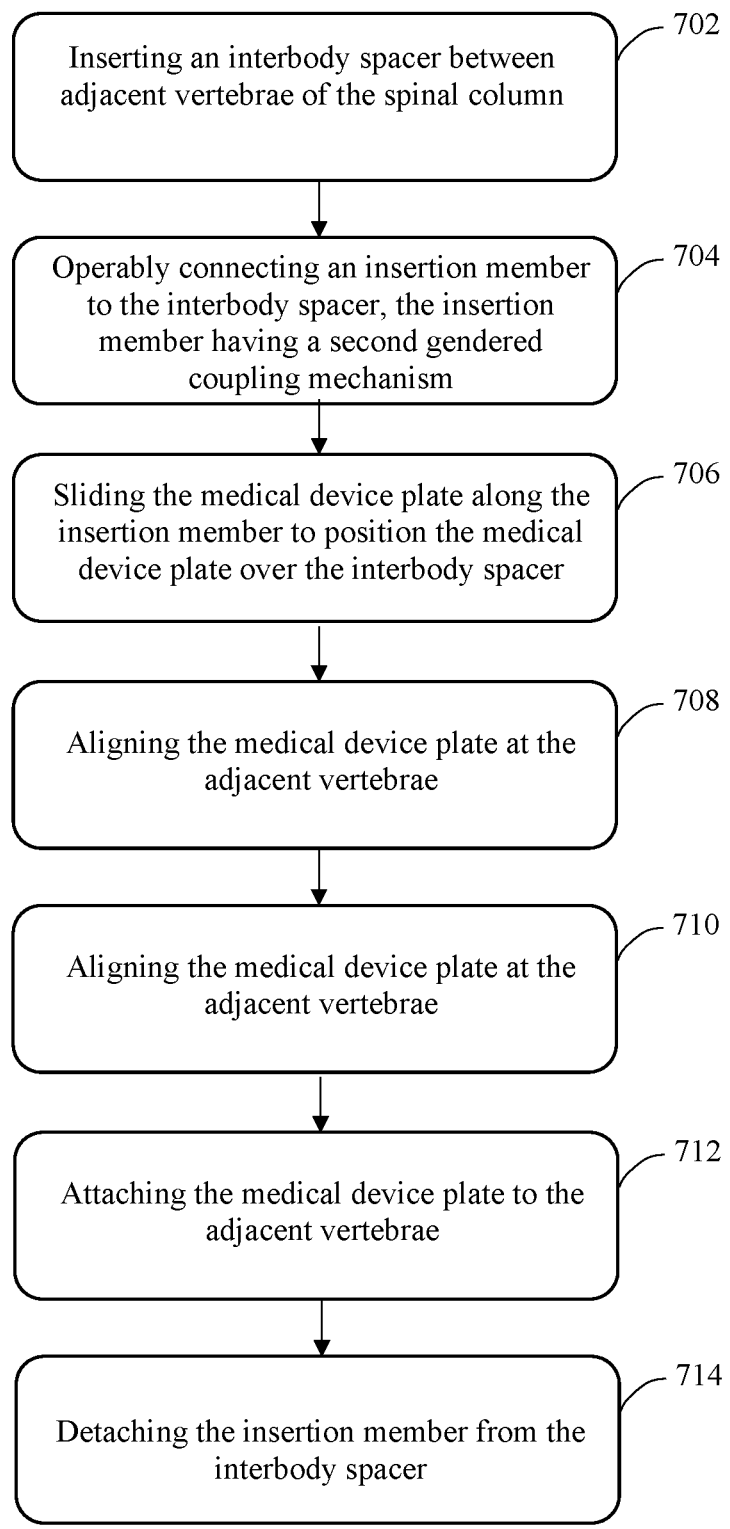
FIG. 7 depicts a flowchart of a method of attaching a medical device plate and interbody spacer to a spinal column in accordance with one embodiment.

FIG. 7 depicts a flowchart of a method 700 for attaching a medical device plate and interbody spacer to a spinal column in accordance with one embodiment. Step 702 involves inserting an interbody spacer between adjacent vertebrae of the spinal column. The interbody spacer of step 702 may be similar to the interbody spacer 102 of FIG. 1 and have a first gendered coupling mechanism.

Step 704 involves operably connecting an insertion member to the interbody spacer, the insertion member having a second gendered coupling mechanism. The gender of the first gendered coupling mechanism is the opposite gender of the second gendered coupling mechanism.

Step 706 involves sliding the medical device plate along the insertion member to position the medical device plate over the interbody spacer. The medical device plate may be similar to the medical device plate 104 of FIG. 1 and include at least one hole or aperture to slide along the length of the insertion member 106. The medical device plate may slide along the insertion member 106 until it comes into contact with the patient's anatomy.

Step 708 involves aligning the medical device plate at the adjacent vertebrae. By virtue of its sliding along the insertion member and coming into contact with the patient's anatomy, the medical device plate may be properly aligned with the patient's anatomy.

Step 710 involves attaching the medical device plate to the adjacent vertebrae. The medical device plate may be secured to the patient's anatomy via one or more screws, for example.

Step 712 involves detaching the insertion member from the interbody spacer. Once the medical device plate is properly secured to patient's anatomy, the insertion member may be removed from the interbody spacer.

In some embodiments, the medical device plate and the spacer may be attached to bone elements other than a spinal column. For example, the medical device plate and an interosseus spacer may be attached to fixate two bone elements of a broken bone.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and devices according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A system comprising:
an interbody spacer having a proximal wall comprising a first coupling mechanism, the interbody spacer configured to be inserted between adjacent vertebrae of a spinal column;
a medical device plate having a plurality of screw holes and at least one non-circular-shaped hole, the medical device plate configured to align with and be attached to at least one vertebra adjacent to the interbody spacer; and
an insertion member comprising a tubular outer member and an inner shaft insertable within and rotatable independent of the outer member,
the outer member comprising a proximal end, and a distal end with a non-circular-shaped perimeter,
the inner shaft comprising a proximal end, and a distal end with a second coupling mechanism, wherein when the inner shaft is fully inserted into the outer member, the proximal end of the inner shaft extends in a proximal direction past the proximal end of the outer member and the distal end of the outer member is positioned adjacent to the second coupling mechanism and the second coupling mechanism is positioned for engagement with the first coupling mechanism;
wherein:
the first coupling mechanism is a male tabbed or a female notched coupling mechanism and the second coupling mechanism is the opposite coupling mechanism to the first coupling mechanism;
the insertion member is configured to be directly connected to the interbody spacer by connecting the first coupling mechanism and the second coupling mechanism;
at least one of (i) the medical device plate is configured to slide via the at least one non-circular-shaped hole over the entirety of the insertion member from the proximal end of the inner shaft the non-circular-shaped perimeter at the distal end of the outer member and be positioned over the interbody spacer and around the distal end of the outer member, or (ii) the non-circular-shaped perimeter of the outer member is inserted into the at least one non-circular-shaped hole of the medical device plate, to prevent rotation of the medical device plate when the medical device plate is adjacent to the interbody spacer; and after the medical device plate is attached to the at least one vertebra adjacent to the interbody spacer, the insertion member is configured to be detached from the interbody spacer and the medical device plate by disconnecting the first coupling mechanism and the second coupling mechanism.

2. The method of claim 1, wherein the distal end of the outer member comprises a hexagonal-shaped perimeter, and wherein the non-circular-shaped hole of the medical device plate comprising a hexagonal-shaped hole.

3. The system of claim 1, wherein the first coupling mechanism is the female notched coupling mechanism.

4. The system of claim 1, wherein the first coupling mechanism is the male tabbed coupling mechanism.

5. The system of claim 1, wherein the medical device plate is configured to be attached to the at least one vertebra adjacent to the interbody spacer with at least one screw.

6. The system of claim 1, wherein a material of the interbody spacer comprises at least one of a plastic, ceramic, metal, autograft, or allograft.

7. The system of claim 1, wherein the insertion member can be pinched to disconnect the insertion member from the interbody spacer.

8. The system of claim 1, wherein the interbody spacer is at least one of a cervical, thoracic, and lumbar spacer.

9. The system of claim 1, wherein the medical device plate is in contact with a plurality of interbody spacers simultaneously and configured to attach to a plurality of vertebrae adjacent to the plurality of interbody spacers.

10. The system of claim 1, wherein the outer member has a similarly shaped non-circular cross section at the proximal end and near the distal end.

11. A method comprising:
inserting an interbody spacer between adjacent vertebrae of a spinal column, the interbody spacer having a proximal wall comprising a first coupling mechanism;
connecting an insertion member directly to the interbody spacer,
the insertion member comprising a tubular outer member and an inner shaft insertable within and rotatable independent of the outer member, the outer member comprising a proximal end, and a distal end with a non-circular-shaped perimeter, the inner shaft comprising a proximal end, and a distal end with a second coupling mechanism,
wherein the first coupling mechanism is a male tabbed or a female notched coupling mechanism and the second coupling mechanism is the opposite coupling mechanism from the first coupling mechanism, and wherein the insertion member is directly connected to the interbody spacer by connecting the first coupling mechanism and the second coupling mechanism;
at least one of (i) sliding a medical device plate via at least one non-circular-shaped hole therein along the entirety of the insertion member from the proximal end of the inner toward the non-circular-shaped perimeter at the distal end of the outer member to position the medical device plate over the interbody spacer and around the distal end of the outer member, or (ii) inserting the non-circular shaped perimeter of the outer member into the at least one non-circular-shaped hole of the medical device plate preventing rotation of the medical device plate when the medical device plate is adjacent to the interbody spacer;
aligning the medical device plate with at least one vertebra adjacent to the interbody spacer;
attaching the medical device plate to the at least one vertebra adjacent to the interbody spacer; and
detaching the insertion member from the interbody spacer.

12. The method of claim 11, wherein the distal end of the outer member comprises a hexagonal-shaped perimeter, and wherein the non-circular-shaped hole of the medical device plate comprising a hexagonal-shaped hole.

13. The method of claim 11, wherein the first coupling mechanism is the female notched coupling mechanism.

14. The method of claim 11, wherein the first coupling mechanism is the male tabbed coupling mechanism.

15. The method of claim 11, wherein the medical device plate is attached to the at least one vertebra adjacent to the interbody spacer with at least one screw.

16. The method of claim 11, further comprising:
removing the insertion member from the at least one non-circular-shaped hole in the medical device plate; and
exposing the at least one non-circular-shaped hole in the medical device plate; and
wherein the step of attaching the medical device plate to the at least one vertebra adjacent to the interbody spacer comprises attaching the medical device plate to the at least one vertebra adjacent to the interbody spacer at the exposed hole.

17. The method of claim 11, wherein the interbody spacer is at least one of a cervical, thoracic, or lumbar spacer.

18. The method of claim 11, wherein the medical device plate is in contact with a plurality of interbody spacers simultaneously to attach the medical device plate with a plurality of vertebrae adjacent to the plurality of interbody spacers.

19. A system comprising:
an interosseous spacer having a proximal wall comprising a first coupling mechanism, the interosseous spacer configured to be inserted between two or more bone elements;
a medical device plate having a plurality of screw holes and at least one non-circular-shaped hole, the medical device plate configured to align with and be coupled to the two or more bone elements adjacent to the interosseous spacer; and
an insertion member comprising a tubular outer member and an inner shaft insertable within and rotatable independent of the outer member, the outer member comprising a proximal end, and a distal end with a non-circular-shaped perimeter, the inner shaft comprising a proximal end, and a distal end with a second coupling mechanism
wherein when the inner shaft is fully inserted into the outer member, the proximal end of the inner shaft extends in a proximal direction past the proximal end of the outer member and the distal end of the outer member is positioned adjacent to the second coupling mechanism;
wherein:
the first coupling mechanism is a male threaded, a female threaded, a male tabbed or a female notched coupling mechanism and the second coupling mechanism is the opposite coupling mechanism from the first coupling mechanism;
the insertion member is configured to be directly connected to the interosseous spacer by connecting the first coupling mechanism and the second coupling mechanism;

at least one of (i) the medical device plate is configured to slide via the at least one non-circular-shaped hole over the entirety of the insertion member from the proximal end of the inner shaft the non-circular-shaped perimeter at the distal end of the outer member and be positioned over the interosseous spacer and align with and be coupled to the two or more bone elements and around the distal end of the outer member, or (ii) the non-circular-shaped perimeter of the outer member is inserted into the at least one non-circular-shaped hole of the medical device plate, to prevent rotation of the medical device plate when the medical device plate is adjacent to the interosseous spacer; and after the medical device plate is coupled to the two or more bone elements, the insertion member is configured to be detached from the interosseous spacer and the medical device plate by disconnecting the first coupling mechanism and the second coupling mechanism.

20. The system of claim 19, wherein the distal end of the outer member comprises a hexagonal-shaped perimeter, and wherein the non-circular-shaped hole of the medical device plate is a hexagonal-shaped hole.

21. A system comprising:
an interbody spacer having a proximal wall comprising a first coupling mechanism, the interbody spacer configured to be inserted between two adjacent vertebrae of a spinal column;
a medical device plate having a plurality of screw holes and at least one non-circular-shaped hole, the medical device plate configured to align with and be coupled to at least one of the vertebrae adjacent to the interbody spacer; and
an insertion member comprising an inner shaft and a tubular outer member,
wherein the inner shaft is configured to sit within and be rotatable independent of the outer member,
wherein the inner shaft includes a proximal end, and a distal end with a second coupling mechanism, wherein the distal end of the inner shaft is narrower than the proximal end of the inner shaft,
wherein the outer member includes a proximal end, and a distal end with a non-circular-shaped perimeter, wherein when the inner shaft is fully inserted into the outer member, the proximal end of the inner shaft extends in a proximal direction past the proximal end of the outer member and the distal end of the outer member is positioned adjacent to the distal end of the inner shaft and the second coupling mechanism,
wherein:
the first coupling mechanism is a male threaded or a female threaded coupling mechanism and the second coupling mechanism is the opposite coupling mechanism to the first coupling mechanism;
the insertion member is configured to be directly connected to the interbody spacer by connecting the first coupling mechanism and the second coupling mechanism;
the medical device plate is configured to slide via the at least one non-circular-shaped hole over the entirety of the insertion member from the proximal end of the inner shaft to the non-circular-shaped perimeter at the distal end of the outer member and be positioned over the interbody spacer and to align with and be connected to the at least one vertebra adjacent to the interbody spacer; and
after the medical device plate is coupled to the at least one vertebra adjacent to the interbody spacer, the insertion member is configured to be detached from the interbody spacer and the medical device plate by disconnecting the first coupling mechanism and the second coupling mechanism.

22. The system of claim 21, wherein the distal end of the outer member comprises a hexagonal-shaped perimeter, and wherein the non-circular-shaped hole of the medical device plate is a hexagonal-shaped hole.

23. The system of claim 21, wherein the outer member has a similarly shaped non-circular cross section at the proximal end and near the distal end.

24. A method comprising:
inserting an interbody spacer between adjacent vertebrae of a spinal column, the interbody spacer having a proximal wall comprising a first coupling mechanism;
connecting an insertion member directly to the interbody spacer,
the insertion member comprising a tubular outer member and an inner shaft insertable within and rotatable independent of the outer member, the outer member comprising a proximal end, and a distal end with a non-circular-shaped perimeter, the inner shaft comprising a proximal end, and a distal end with a second coupling mechanism,
wherein the first coupling mechanism is a male threaded, a female threaded, a male tabbed or a female notched coupling mechanism and the second coupling mechanism is the opposite coupling mechanism from the first coupling mechanism,
and wherein the insertion member is directly connected to the interbody spacer by connecting the first coupling mechanism and the second coupling mechanism;
sliding a medical device plate via at least one non-circular-shaped hole therein along the entirety of the insertion member from the proximal end of the inner shaft toward the non-circular-shaped perimeter at the distal end of the outer member to position the medical device plate over the interbody spacer,
wherein the non-circular-shaped perimeter of the outer member is inserted into the at least one non-circular-shaped hole of the medical device plate preventing rotation of the medical device plate when the medical device plate is adjacent to the interbody spacer;
aligning the medical device plate with at least one vertebra adjacent to the interbody spacer;
coupling the medical device plate to the at least one vertebra adjacent to the interbody spacer with at least one screw; and
detaching the insertion member from the interbody spacer.

25. The system of claim 24, wherein the distal end of the outer member comprises a hexagonal-shaped perimeter, and wherein the non-circular-shaped hole of the medical device plate is a hexagonal-shaped hole.

* * * * *